United States Patent [19]
Hays

[11] Patent Number: 5,277,202
[45] Date of Patent: Jan. 11, 1994

[54] EASY FIT ANTI-SNORING DEVICE

[75] Inventor: Marvin B. Hays, Albuquerque, N. Mex.

[73] Assignee: MB Hays, Inc., N. Mex.

[21] Appl. No.: 935,290

[22] Filed: Aug. 26, 1992

[51] Int. Cl.$^5$ ............................ A61F 5/56; A61C 5/14
[52] U.S. Cl. .................................... 128/848; 128/861; 128/862; 602/902
[58] Field of Search .................... 128/859–862, 848; 602/902; 2/2

[56] References Cited

U.S. PATENT DOCUMENTS

| | | | |
|---|---|---|---|
| 1,674,336 | 6/1928 | King | 128/861 |
| 2,483,157 | 9/1949 | Singer | 128/861 |
| 2,669,988 | 2/1954 | Carpenter | 128/861 |
| 2,857,909 | 10/1958 | Johnson | 128/861 |
| 3,126,002 | 3/1964 | Owens | 128/861 |
| 4,185,817 | 1/1980 | Peterson | 128/861 |
| 4,955,393 | 9/1990 | Adell | 128/859 |
| 5,092,346 | 3/1992 | Hays | 128/861 |
| 5,174,284 | 12/1992 | Jackson | 128/859 |

*Primary Examiner*—Michael A. Brown
*Attorney, Agent, or Firm*—Cushman, Darby & Cushman

[57] ABSTRACT

A dental orthosis is provided for use in the treatment of snoring. The upper portion of the device defines a trough for receiving some of the upper teeth of the patient. The rear wall of the trough is truncated so that the device can accommodate both narrow and wide dental arches so that one size of the device can accommodate substantially all users. Once inserted into the mouth the device snugly engages the upper teeth, particularly the front teeth, and remains positioned independent of natural motions of the lower jaw. The lower portion of the device is formed into a ramp structure whereby natural jaw motions result in the engagement of the lower teeth with the ramp, which will cam the lower jaw into a more forward position.

14 Claims, 1 Drawing Sheet

EASY FIT ANTI-SNORING DEVICE

BACKGROUND OF THE INVENTION

1. Field of the Invention

This invention relates to a device for reducing or preventing snoring and, in particular, to an anti-snoring device which can be easily fit to patients having either a wide or a narrow dental arch.

2. Description of the Related Art

Snoring is normally the result of vibration of the uvula, soft palate, and adjacent structures during sleep and signals partial obstruction due to the narrowing of the upper airway at that site. In most cases, breathing is normal or only minimally impaired, and symptoms primarily concern sleep disturbance and the social consequences of snoring. In other cases, snoring is associated with the obstructive sleep apnea syndrome, a serious condition characterized by intermittent upper airway obstructions that require arousal for relief.

Various devices are known in the art for placement in the oral cavity and intended for to reduce snoring. Some investigators have provided devices which are arranged to seal the lips of the wearer, one to another, thus blocking air passage through the mouth. Others have recognized that portions of the uvula, soft palate, and adjacent structures vibrate during sleep, in response to the passage of air past these tissues, and attempt to minimize such vibrations by providing devices which sharply reduce the volume of air passing through the mouth, without necessarily completely blocking the mouth. However, if the nose is blocked, or partially blocked, this reduction of the airway increases the velocity of the air passing those tissues and snoring can actually increase.

Yet another type of prior art device is exemplified by the device of U.S. Pat. No. 1,674,336 to King. King intends that his device will maintain a plentiful supply of oxygen to the blood of a user during sleep, and even reduce snoring. His structure comprises an upper channel and a lower channel to receive the upper and lower teeth, respectively. The two channels are spaced apart vertically to prop the upper and lower front teeth apart and to define an air passage therebetween. Thus, in use, the device props the teeth of a user apart in a fixed position, which King claims opens the posterior airway to facilitate the passage of air to and from the throat and lungs. As the device receives the top and bottom teeth and fixes their relative position, natural mouth motions, including motion of the lower jaw, are prevented.

A device which effectively alleviates or prevents snoring is disclosed in my earlier U.S. Pat. No. 5,092,346 for a Dental Orthosis for Alleviation of Snoring, marketed under the name Snore Guard®, the disclosures of which is incorporated herein by this reference. That structure includes an upper portion in the form of pair of parallel and substantially coextensive walls defining a trough corresponding in shape to the curvature of the patient's upper dental arch, for receiving the upper teeth of the patient. Once properly fitted, the device will snugly receive the front teeth and the premolars and remain positioned independent of natural motions of the lower jaw.

The lower portion of the '346 patent device is formed into a ramp structure whereby natural jaw motions result in the engagement of the lower teeth against the ramp, which will cam the lower jaw into a more forward position. An aperture in the device between the upper and lower portions facilitates the passage of air for mouth breathing and attracts the tongue forward. By inducing the lower jaw and tongue to a more forward position, the device induces a more open posterior airway in the patient, resulting in a significant reduction in snoring.

In contradistinction to the teachings of King, the structure of the '346 patent device does not fix the position of the upper and lower jaw and tongue. Instead, by an adroit arrangement of the structure, the device snugly attaches to the upper teeth and jaw, while allowing natural mouth movements including motions of the lower jaw and teeth, and tongue. That device is further distinguished in providing the ramp to engage the lower anterior teeth and induce forward movement of the lower jaw, resulting in the opening of the posterior airway.

SUMMARY OF THE INVENTION

Thus, the '346 patent device was a significant improvement in the art over devices of the type disclosed in King. That is not to say, however, that improvements in the '346 patent device are not possible, and, in fact, the present invention constitutes an improvement in that device.

More particularly, I discovered that, because the '346 patent device provided substantially co-extensive upper trough defining walls which were curved to accommodate the patient's dental arch, a particular configuration of the device may only be fit to a certain range of dental arch sizes and shapes. Thus, custom molding of the device and/or maintenance of a relatively large inventory of the '346 device may be required to accommodate a variety of patients.

Thus, it was an object of the invention to provide an anti-snoring device generally of the type disclosed in the '346 patent, but which could accommodate a variety of dental arch sizes and shapes so that a single size or a few sizes can accommodate all users, thereby eliminating the need for a large inventory and the time and cost of custom fitting.

The foregoing object is achieved in accordance with the invention by providing a device having an upper portion which is defined by an arching front wall and a truncated rear wall which is substantially parallel to the front wall but which extends through an arch substantially smaller than that of the front wall. I found that a reduction in the rear wall of the upper trough allowed a device of a given size to be fit to patients having a variety of dental arch sizes and shapes. Further, I found that, surprisingly, despite the significant reduction in the arch length of the rear wall of the upper trough, a snug fit, irrespective of the dental arch, was possible and the device could still remain positioned independent of natural motions of the lower jaw. Thus, like the '346 device, the ramp structure of the lower portion of the device allows natural jaw motions, including the bite reflex and, upon engagement of the user's lower teeth against the ramp, will cam the lower jaw into a more forward position, thereby achieving the advantages of that structure. However, because the device disclosed hereinafter does not require custom fitting to the upper portion to the patient's dental arch, the device can accommodate the physiology of a variety of patients.

Other objects, features, and characteristics of the present invention as well as the methods of operation and functions of the related elements of structure, and the combination of parts and economies of manufacture, will become more apparent upon consideration of the following description and the appended claims with reference to the accompanying drawings, all of which form a part of this specification, wherein like reference numerals designate corresponding parts in the various figures.

DETAILED DESCRIPTION OF THE PREFERRED EMBODIMENTS

As illustrated in FIGS. 1-5, the dental orthosis 10 for reducing snoring in accordance with the present invention comprises a structure shaped to generally conform to the upper dental arch of a user and extending at least between the pre-molar teeth on each side of the wearer's mouth.

The main body 12 of the device may be formed from a single piece of methylmethacrylate, which is a plastic material used for dentures. If formed of methylmethacrylate, the device must then be cured to prevent absorption of mouth fluids, or cleaning fluids, and to present a smooth non-irritating surface to the soft tissues of the mouth.

However, the main body 12 of the device is most preferably composed of a resilient semi-rigid polycarbonate resin thermoplastic having good physical characteristics and having a specific gravity of about 1.20, a tensile strength (yield) of about 9000 and a softening temperature of about 310 degrees F. An example such resin is sold by the General Electric Company under the Registered Trademark LEXAN. The material provides a framework for the device, and it is preferably used in conjunction with an additional resin material as further discussed below.

In the preferred embodiment, a substantial advantage to the user is offered when another resin layer 14, 16 is bonded to the polycarbonate resin thermoplastic device described above, such layer 14, 16 preferably composed of an ethylene-vinyl acetate copolymer resin having a softening and molding temperature of between about 125 and 175 degrees F and most preferably about 150 degrees F. An example of such resin is sold by Du Pont Company under the Registered Trademark ELVAX.

As will later be more fully explained, the preferred embodiment is self fitting, for both narrow and wide arches, so that one size of the device will accommodate all or substantially all users. This saves time and money as no custom molding and fitting is required, thereby eliminating the need for a variety of molds and the services of a dental laboratory in fitting the device to a particular patient.

Figure 1:
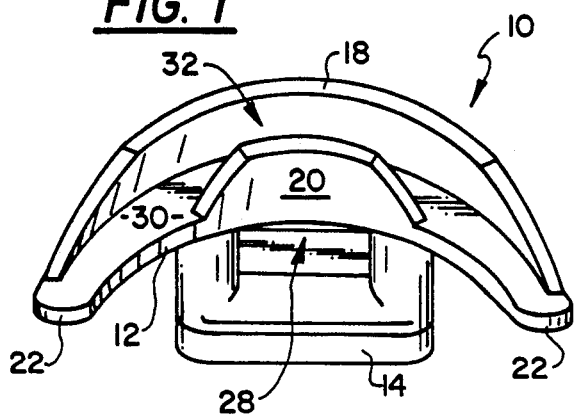
FIG. 1 is a perspective view from the rear of a dental orthosis provided in accordance with the invention with the resin material omitted from the tooth receiving trench, for clarity.
Figure 2:
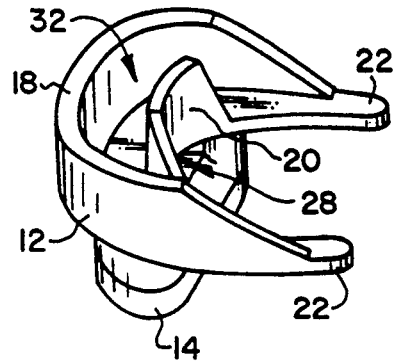
FIG. 2 is a side elevation of the device of FIG. 1 with the resin material omitted from the tooth receiving trench, for clarity.
Figure 3:
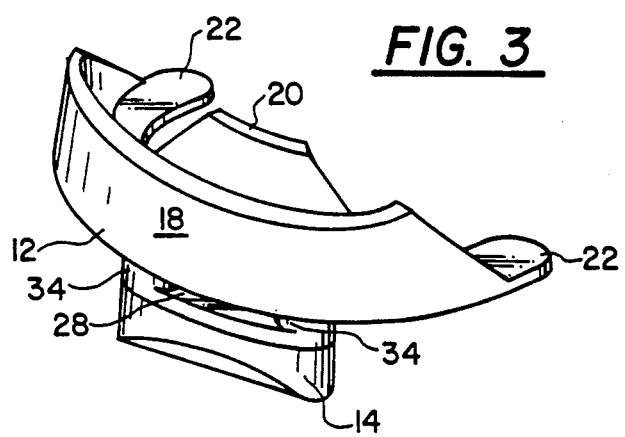
FIG. 3 is a perspective view from the forward side of the device of FIG. 1 with the resin material omitted from the tooth receiving trench, for clarity.

Considering now FIGS. 1 and 2, the dental orthosis 10 comprises a semicircular structure, more specifically an arch, having an outer or forward wall 18 corresponding generally to the curvature of an upper dental arch, and a truncated rearward wall 20, which define therebetween a teeth receiving trench 32. In the illustrated embodiment, truncated rearward wall 20 has an upper edge of about 15 mm in arch length and a lower edge portion adjacent the base of the trough of about 25 mm in arch length. The rearward side edges are inclined downwardly from the upper edge to the lower edge portion at an angle of 45 to 60 degrees to intersect with ends 22.

A ramp structure 24 extends laterally between the lower extremities of wall 12. The ramp structure includes a ramp element 26 defined as a portion of the main body 12 which extends rearwardly at an angle of about 60°.

An aperture 28 extends through the device as detailed below. The bottom 30 of the trench 32 is substantially horizontal when the device 10 is in use.

More particularly, in order to form a more generous air passage 28 a pair of stanchions 34 join the ramp element 26 to the upper portion of the main body. The ramp element 26 may be configured as deemed necessary or desirable for ease of application and durability of the acetate copolymer resin layer 14. In the alternative, the ramp element 26 has uniform upper and lower surfaces. An aperture, or a series of apertures may be provided to facilitate the application of the resin layer 14 to increase its durability on the structure.

Figure 4A:
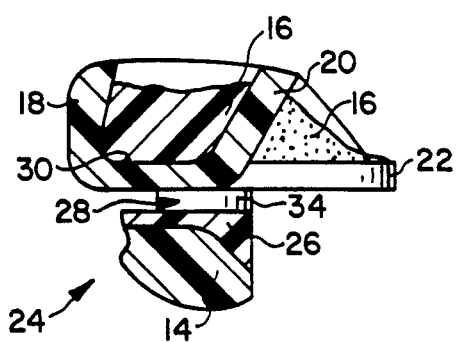
FIG. 4A is a cross-section side view of the device of FIG. 1.
Figure 4B:
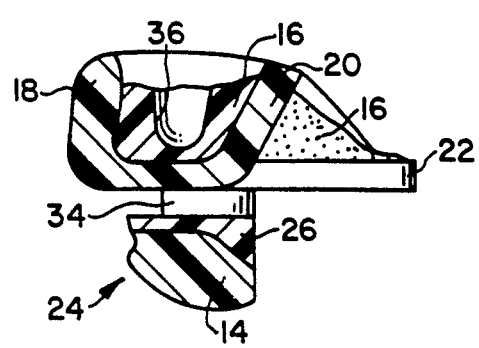
FIG. 4B is a view similar to FIG. 5A, showing an impression made by a patient's teeth once the device has been fitted to that patient.

The resin layer previously described is shown by reference to FIGS. 4A and 4B, which is a cross section of the device of FIGS. 1-4. A layer of acetate copolymer resin 16 is shown applied to the teeth receiving trench 32 and to the ramp element 26. FIG. 4B is the same cross-sectional view as found in FIG. 4A. The only difference is that FIG. 4B shows a tooth impression 36 in the acetate copolymer resin layer resulting from the fitting of the device to the patient.

The lower anterior teeth of the user engage the device only at a ramp surface of ramp structure 24 whereby natural lower jaw and teeth motions are preserved. Thus, the lower anterior teeth naturally engage the ramp structure 24 and are induced by natural jaw movements to advance along the ramp structure 24 moving the lower jaw into a more forward position.

When the device is formed from the polycarbonate resin-thermoplastic having the layer of acetate copolymer resin bonded thereto at the teeth-engaging surfaces, namely the trench which receives the upper teeth and the ramp which receives the lower teeth, then individual fitting of the device to the user is greatly simplified, as is user comfort. The acetate copolymer resin layer 16 is about 3 to 4 millimeters in thickness in the trench 32 and a coating 14 of approximately 2 to 3 millimeters thick is applied to the ramp element 26. The acetate copolymer resin has a substantially lower softening and molding temperature than that of the polycarbonate resin-thermoplastic forming the main body of the device and thus individual fitting to the user's mouth is simplified. An immersion of the device in a hot fluid, preferably water, prior to the fitting serves to soften the acetate copolymer resin layer whereby it accepts the users distinctive tooth configuration during the fitting process. Upon cooling to ambient temperature, the acetate copolymer resin retains the user's tooth configuration, for ease of repeat placement by the user. Excess resin can be cut from the device to make the device more comfortable to use. Additional minor adjustment may be advisable to increase comfort for the user or to modify the alignment of the device. If extensive dental work is later performed or if mechanical damage occurs, a new fitting may be necessary for mechanical comfort and ease of use.

It is also important to note that relatively minor forward movement of the jaw, in the range of 2 to 6 mm, serves to reduce the incidence of snoring. As is the case with any orthosis, further adjustment of the device to the user may be desirable from time to time.

Considering again the Figures the dental orthosis comprises a semicircular structure, more specifically an arch, comprising a front wall 18 and a truncated rear wall 20. The front and rear walls are essentially parallel. In order to accommodate users having a variety of dental arch shapes and widths, rear wall 20 has an arch length substantially less than that of wall 18. As is apparent from the foregoing and as can be seen from FIG. 1, in particular, to achieve the objects of the invention, the angle transcribed by the rear wall is substantially less than the angle transcribed by the front wall. Thus, the rear wall lies behind the front teeth and the front teeth are snugly received between the front and rear walls, preferably in the relatively soft filler material 16, as described above. The rear wall terminates laterally, rearwardly in edges which slope downwardly at an angle of about 45 to 60 degrees to intersect ends 22, as noted above. The device can thus be fit to a patient substantially irrespective of the disposition and arch of the patient's upper teeth rearwardly of the front teeth and, substantially irrespective of the curvature of the user's dental arch, the device will be snugly retained in proper position in the mouth.

In accordance with the invention, then, with only a single or relatively few sizes in inventory, the device can be fitted to the patient by a dentist in a matter of minutes. With proper instructions and safeguards, the device could also be self-fitted by the patient.

While the invention has been described in connection with what is presently considered to be the most practical and preferred embodiment, it is to be understood that the invention is not to be limited to the disclosed embodiment, but on the contrary is intended to cover various modifications and equivalent arrangements included within the spirit and scope of the appended claims.

What is claimed is:

1. A device for placement in the mouth to cam the lower jaw forward to thereby reduce snoring by a user, comprising:

an upper element having a curved shape which generally corresponds to the shape of an upper dental arch, said upper element having a forward wall having a first length, a truncated rearward wall having a second length which is substantially less than said first length which is substantially less than said first length such that an angle transcribed by said rearward wall is substantially less than an angle transcribed by said forward wall, and a bottom wall disposed in a substantially horizontal plane from said forward wall rearwardly and having a length substantially equal to or greater than said first length, said reward wall has a length substantially less than said bottom wall; said forward wall, said truncated rearward wall, and said bottom wall defining therebetween an upwardly open tooth receiving trench for receiving at least a portion of at least some of the upper teeth of the user; and a ramp means extending downwardly from said upper element, including a ramp element, said ramp means defining a ramp surface for engaging at least some of the lower anterior teeth of the patient, said ramp element being operatively coupled to said upper element so that when the upper teeth of the patient are received in the tooth receiving trench of the upper element, the ramp surface is offset with respect to a plane of the lower anterior teeth when the lower jaw is in an unstressed position so that engagement with said ramp surface by said lower teeth positively shifts the lower jaw forward with respect to said unstressed position.

2. A device as in claim 1, further comprising means defining an aperture for allowing the passage of air into and out of the patient's oral cavity.

3. A device as in claim 2, wherein said aperture means is defined between said upper element and said ramp means.

4. A device as in claim 1, composed of a resilient semi-rigid polycarbonate resin thermoplastic body having a specific gravity of about 1.2, tensile strength (yield) of about 9,000 PSI, and a softening temperature of about 310 degrees fahrenheit.

5. A device as in claim 4, further comprising a layer bonded to at least a portion thereof, said layer being composed of an ethylene-vinyl acetate copolymer resin having a softening and molding temperature of about 150 degrees fahrenheit.

6. A device as in claim 5, wherein said layer is about 3 millimeters in thickness.

7. A device as in claim 5, wherein said layer is bonded to an interior surface of at least part of said trench and to at least a portion of said ramp element.

8. A method of fitting a dental orthosis that reduces snoring during sleep, comprising the steps of:

guiding into a patient's oral cavity a pre-formed device which includes:

an upper element having a curved shape which generally corresponds to the shape of an upper dental arch, said upper element having a forward wall having a first length, a truncated rearward wall having a second length which is substantially less than said first length such that an angle transcribed by said rearward wall is substantially less than an angle transcribed by said forward wall, and a bottom wall disposed in a substantially horizontal plane from said forward wall rearwardly and having a length substantially equal to or greater than said first length, said reward wall has a length substantially less than said bottom wall; said forward wall, said truncated rearward wall, and said bottom wall defining therebetween an upwardly open tooth receiving trench for receiving at least a portion of at least some of the upper teeth of the user; and a ramp means extending downwardly from said upper element, including a ramp element, said ramp means defining a ramp surface for engaging at least some of the lower anterior teeth of the patient, said ramp element being operatively coupled to said upper element so that when the upper teeth of the patient are received in the tooth receiving trench of the upper element, the ramp surface is offset with respect to a plane of the lower anterior teeth when the lower jaw is in an unstressed position so that engagement with said ramp surface by said lower teeth positively shifts the lower jaw forward with respect to said unstressed position;

introducing the patient's upper teeth into said tooth receiving trench; and allowing the patient's lower teeth to engage the ramp surface of the ramp element, thereby shifting the lower jaw forwardly with respect to said unstressed position so as to increase an air passage through the oral cavity.

9. A method as in claim 8, wherein said step of allowing comprises allowing a lower jaw bite reflex and teeth motions against the ramp element to thereby move the lower jaw forward to increase spacing between the tongue and palate and uvula.

10. A self fitting dental orthosis for removable placement in the mouth and for engaging the upper and lower teeth of a user, comprising a main body element consisting essentially of:

an upper element having a curved shape which generally corresponds to the shape of an upper dental arch, said upper element having a forward wall having a first length, a truncated rearward wall having a second length which is substantially less than said first length such that an angle transcribed by said rearward wall is substantially less than an angle transcribed by said forward wall, and a bottom wall disposed in a substantially horizontal plane from said forward wall rearwardly and having a length substantially equal to or greater than said first length, said reward wall has a length substantially less than said bottom wall; said forward wall, said truncated rearward wall, and said bottom wall defining therebetween an upwardly open tooth receiving trench for receiving at least a portion of at least some of the upper teeth of the user;

a ramp means extending downwardly from said upper element, including a ramp element, said ramp means defining a ramp surface for engaging at least some of the lower anterior teeth of the patient, said ramp element being operatively coupled to said upper element so that when the upper teeth of the patient are received in the tooth receiving tooth trench of the upper element, the ramp surface is offset with respect to a plane of the lower anterior teeth when the lower jaw is in an unstressed position so that engagement with said ramp surface by said lower teeth positively shifts the lower jaw forward with respect to said unstressed position; and an aperture defined therethrough for allowing air to pass into and out of the mouth.

11. A device as in claim 10, wherein said main body is composed of a resilient semi-rigid polycarbonate resin thermoplastic body having a specific gravity of about 1.2, a tensile strength (yield) of about 9,000 PSI, and a softening temperature of about 310 degrees Fahrenheit.

12. A device as in claim 11, wherein at least a portion of said body has a layer bonded thereto, said layer being composed of an ethylene-vinyl acetate copolymer resin having a softening and molding temperature of about 150 degrees Fahrenheit.

13. A device as in claim 12, wherein said layer is about 3 millimeters in thickness.

14. A device as in claim 12, wherein said layer is bonded to a interior surface of at least part of said trench and to at least a portion of said ramp element.

* * * * *